US007125550B2

(12) United States Patent
Herr et al.

(10) Patent No.: US 7,125,550 B2
(45) Date of Patent: Oct. 24, 2006

(54) HUMAN SPERM SPECIFIC LYSOZYME-LIKE PROTEINS

(75) Inventors: John C. Herr, Charlottesville, VA (US); Friederike Jayes, Cary, NC (US); Arabinda Mandal, Charlottesville, VA (US); Jagathpala Shetty, Charlottesville, VA (US); Michael J. Wolkowicz, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 134 days.

(21) Appl. No.: 10/181,611

(22) PCT Filed: Jan. 19, 2001

(86) PCT No.: PCT/US01/01716

§ 371 (c)(1),
(2), (4) Date: Jul. 18, 2002

(87) PCT Pub. No.: WO01/53487

PCT Pub. Date: Jul. 26, 2001

(65) Prior Publication Data

US 2003/0129652 A1    Jul. 10, 2003

Related U.S. Application Data

(60) Provisional application No. 60/251,759, filed on Dec. 7, 2002, provisional application No. 60/176,884, filed on Jan. 19, 2000.

(51) Int. Cl.
*A61K 39/395* (2006.01)
*A61K 39/40* (2006.01)
*A61K 39/42* (2006.01)
*C12N 5/00* (2006.01)
*C12N 5/02* (2006.01)

(52) U.S. Cl. ............... 424/152.1; 424/139.1; 424/143.1; 435/387.1; 435/388.1; 435/389.1; 514/841

(58) Field of Classification Search ............... 435/226, 435/206; 424/811
See application file for complete search history.

(56) References Cited

U.S. PATENT DOCUMENTS 5,602,005 A    2/1997   Herr et al.
5,830,472 A   11/1998   Herr et al.

FOREIGN PATENT DOCUMENTS

WO    WO 00/28045    5/2000
WO    WO 01/00806    1/2001
WO    WO 02/00691    1/2002
WO    WO 01/59132    8/2002

OTHER PUBLICATIONS

Swissprot Data Base Acc#A40729 Yeh et al, Dec. 5, 1997, Alignment with SEQ ID NO: 2.*
Issued Patents Data Base US6,548,633 Dumas et al Apr. 15, 2003 (priority date Dec. 22, 1998). Alignment with SEQ ID No. 2.*
O'Rand et al Designing an effective immunocontraceptive. J Reprod Immunol. Nov. 30, 1997;36(1-2):51-9. Review.*
Lea et al A chimeric sperm peptide induces antibodies and strain-specific reversible infertilty in mice. Biol Reprod. Sep. 1998;59(3):527-36.*
Frayne et al The potential use of sperm antigens as targets for immunocontraception; past, present and future, J Reprod Immunol. May 1999;43(1):1-33. Review.*
DataBased Medline EMBASE Biosis Caplus via Winsock to STN. Art search Apr. 9, 2005.*
Naz, Rajesh K: "Application of Sperm Antigens in Immunocontraception", Frontiers in Bioscience 1, e87-95 Sep. 1, 1996.
Shetty, Jagathpala et al.: "Human Sperm Proteome: Immunodominant Sperm Surface Antigens Identified with Sera from Infertile Men and Women", Biology of Reproduction, vol. 61, pp. 61-69, (1999).
Database EMBL 'Online!, Accession No. Z98304.1, Aug. 11, 1997, Grafham, D..: "Human DNA sequence from clone RPI-54B20 on chromosome Xp1-11.3. Contains . . . the gene for a novel protein similar to lysozyme . . . ".
Database EMBL 'Online!, Accession No. AQ345840, Jan. 25, 1995, Zhao, S. et al., "RPC111-126G23.TJ RPCI-1 I *Homo sapiens* genomic clone RPCI-11-126G23, genomic survey sequence".
Database EMBL 'Online!, Accession No. BF059393, Oct. 18, 2000, NCI-CGAP: 7k59a01.x1 NCl_CGAP_GC6 *Homo Sapiens* cDNA clone IMAGE: 3479688 3' similar to SW:LYCI_ANAPL . . .
Database EMBL Heidelberg, FRG 'Online!, Accession No. AA393240 May 19, 1997, Hillier, L. et al.: zt74a03.rl Soares_testis_NHT Homosapiens cDNA clone.
Database EMBL Heidelberg, FRG 'Online, Accession No. A1190761, Oct. 14, 1998, NCI-CGAP: qd61c06.xl Soares_testis_NHT *Homo sapiens* cDNA clone.
Database EMBL Heidelberg, FRG 'Online, Accession No. P00705, Jul. 21, 1986, Anas Platyrhynchos, Lysozyme C-1 Precurser (EC 3.2.1.17).

* cited by examiner

*Primary Examiner*—Sheridan Swope
(74) *Attorney, Agent, or Firm*—Rodney L. Sparks

(57) ABSTRACT

The present invention relates to two novel, testis-specific proteins (C19 and C23) that arc lysozyme paralogues. The proteins are believed to play a role in capacitation of sperm and the fertilization of the ovum. Therefore these compounds make ideal targets for the design of contraceptive agents. The C19 and C23 proteins can also be modified to establish lysozyme activity and the modified proteins can then be used in all applications that currently exist for lysozymes.

2 Claims, 3 Drawing Sheets

FIG. 2

```
 1. C19               KLYGRCELARVLHDFGLDGYRGYSLADWCLAYFTSGFNAAALDYEADGSTDNGIFQINSRRWCSN    (SEQ ID NO: 2)
 2. Langur blood      KIFERCELARTLKKLGLDGYKGVSLANWVCLAKWESGYNTEATNYNPDESTDYGIFQINSRYWCNN   (SEQ ID NO: 12)
 3. Langur stomach    KIFERCELARTLKKLGLDGYKGVSLANWVCLAKWESGYNTEATNYNPDESTDYGIFQINSRYWCNN   (SEQ ID NO: 13)
 4. Monkey blood      KIFERCELARTLKRLGLDGYKGVSLANWVCLAKWESGYNTEATNYNPDESTDYGIFQINSRYWCNN   (SEQ ID NO: 14)
 5. Monkey blood      KIFERCELARTLKRLGLDGYRGISLANWVCLAKWESDYNTQATNYNPDQSTDYGIFQINSHYWCNN   (SEQ ID NO: 15)
 6. Langur stomach    KIFERCELARTLKRLGLDGYRGISLANWVCLAKWESGYNTQATNYNPDQSTDYGIFQINSHYWCNN   (SEQ ID NO: 16)
 7. Gorilla blood     KIFERCELARTLKRLGMDGYRGISLANWMCLAKWESGYNTRATNYNADRSTDYGIFQINSRYWCND   (SEQ ID NO: 17)
 8. Human             KVFERCELARTLKRLGMDGYRGISLANWMCLAKWESGYNTRATNYNADRSTDYGIFQINSRYWCND   (SEQ ID NO: 18)
 9. Rabbit kidney     KIYERCELARTLKKLGLDGYKGVSLANWMCLAKWESSYNTRATNYNPDKSTDYGIFQINSRYWCND   (SEQ ID NO: 19)
10. Guereza Stomach   KIFERCELARTLKKLGLDGYKGVSLANWVCLAKWESGYNTDATNYNPDESTDYGIFQINSRYWCNN   (SEQ ID NO: 20)
11. Rhesus m. gland   KIFERCELARTLKRLGLDGYRGISLANWVCLAKWESNYNTQATNYNPDQSTDYGIFQINSHYWCNN   (SEQ ID NO: 21)
    Invariant residues        C          ES                W C              S DYG  Q N    WC 1. C19               LTPNVPNVCRMYCSDLLNPNLKDTVICAMKITQEPQGLGYWEAWRHHCQGKDLTEWVDGCDF
 2. Langur blood      KTPGAVDACHISCSALLQNNIADAVACAKRVVSDPQGVRAWVAWRNHCQNKDVSQYVKGC--
 3. Langur stomach    KTPGAVDACHISCSALLQNNIADAVACAKRVVSDPQGIRAWVAWRNHCQNKDVSQYVKGC--
 4. Monkey blood      KTPGAVDACHISCSALLQNNIADAVACAKRVVSDPQGIRAWVAWRNHCQNRDVSQYVKGC--
 5. Monkey blood      KTPGAVNACRISCNALLQDNIADAVTCAKRVRDPQGIRAWVAWRNHCQNRDVSQYVQGC--
 6. Langur stomach    KTPGAVNACHISCNALLQDNIADAVTCAKRVRDPQGIRAWVAWRNHCQNRDVSQYVQGC--
 7. Gorilla blood     KTPGAVNACHLSCSALLQDNIADAVTCAKRVRDPQGIRAWVAWRNRCQNRDVRQYVQGC--
 8. Human             KTPGAVNACHLSCSALLQDNIADAVTCAKRVRDPQGIRAWVAWRNRCQNRDVRQYVQGC--
 9. Rabbit kidney     KTPRAVNACHIPCSALLKDDITQAVACAKRVVSDPQGIRAWVAWRNHCQNQDLTPYIRGC--
10. Guereza Stomach   KTPGAVNACHISCNALLQNNIADAVACAKRVVSDPQGIRAWVAWKKHCQNRDVSQYVEGC--
11. Rhesus m. gland   KTPGAVNACHISCNALLQDNIADAVTCAKRVVSDPQGIRAWVAWRNHCQNRDVSQYVQGC--
    Invariant residues     C  C            CA           W W   C          C
```

FIG. 3

```
1.  C23              KIYERCELAAARLERAGLNGYKGYGVGDWLCMAHYESGFDTAFVDHNPDGSSEYGIFQLNSAWWCDNGITPTKNLCH
2.  Duck egg white   KVYSRCELAAAMKRLGLDNYRGYSLGNWVCAANYESGFNTQATNRNTDGSTDYGILQINSRWWCDNGKTPrkNACG
3.  Pheasant egg white KVYGRCELAAAMKRLGLDNYRGYSLGNWVCAAKYESNFNTHATNRNTDGSTDYGILQINSRWWCNDGKTPgrNLCH
4.  Duck egg white   KVYSRCELAAAMKRLGLDNYRGYSLGNWVCAANYESSFNTQATNRNTDGSTDYGILEINSRWWCDNGKTPrkNACG
5.  Pheasant egg white KVYGRCELAAAMKRMGLDNYRGYSLGNWVCAAKFESNENTGATNRNTDGSTDYGILQINSRWWCNDGRTPgkNLCH
6.  Chachalaca egg white KIYKRCELAAAMKRYGLDNYRGYSLGNWVCAARYESNYNTQATNRNSNGSTDYGILQINSRWWCNDGRTPgkNLCH
7.  Pheasant egg white KVYGRCELAAAMKRLGLDNYRGYSLGNWVCAAKFESNFNTGATNRNTDGSTDYGILQINSRWWCNDGRTPgkNLCH
8.  Pheasant egg white KVYGRCELAAAMKRLGLDNYRGYSLGNWVCAAKFESNFNTHATNRNTDGSTDYGILQINSRWWCNDGRTPgrNLCH
9.  Pheasant egg white KVYGRCELAAAMKRLGLDNYRGYSLGNWVCAAKFESNFNTHATNRNTDGSTDYGILQINSRWWCNDGRTPgrNLCH
10. Monkey blood     KIFERCELARTLKKLGLDGYKGVSLANWVCLAKWESGYNTEATNYNpdESTDYGIFQINSRYWCNNGKTPgvDACH
11. Langur stomach   KIFERCELARTLKKLGLDGYKGVSLANWVCLAKWESGYNTEATNYNpdESTDYGIFQINSRYWCNNGKTPgvDACH
    Invariant residues             W C         ES                  S   DYG  Q N    WC             C
```

```
1.  C23              MDCHDLLNRHILDDIRCAKQIVSSQNGLSAWTSWRLHCSGHDLSEWLKGCCDMHVKIDPKIHP (SEQ ID NO: 4)
2.  Duck egg white   IPCSVLLRSDITEAVRCAKRIVSDGDGMNAWVAWRNRCRGTDVSKWIRGCRL---------- (SEQ ID NO: 22)
3.  Pheasant egg white IPCSALLSSDITASVNCAKKIVSDGNGMNAWVAWRNRCKGTDVSVWTRGCRL---------- (SEQ ID NO: 23)
4.  Duck egg white   IPCSVLLRSDITEAVKCAKRIVSDGDGMNAWVAWRNRCKGTDVSRWIRGCRL---------- (SEQ ID NO: 24)
5.  Pheasant egg white IPCSALLSSDITASVNCAKKIVSDGNGMNAWVAWRKHCKGTDVNVWIRGCRL---------- (SEQ ID NO: 25)
6.  Chachalaca egg white ISCSSALMGADIAPSVRCAKRIVSDGDGMNAWVAWRKHCKGTDVSTWIKDCKL---------- (SEQ ID NO: 26)
7.  Pheasant egg white IPCSALLSSDITASVNCAKKIVSDGDGMNAWVAWRKHCKGTDVNVWIRGCRL---------- (SEQ ID NO: 27)
8.  Pheasant egg white IPCSALLSSDITASVNCAKKIVSDGNGMNAWVAWRNRCKGTDVNAWTRGCRL---------- (SEQ ID NO: 28)
9.  Pheasant egg white IPCSALLSSDITASVNCAKKIVSDRNGMNAWVAWRNRCKGTDVNAWIRGCRL---------- (SEQ ID NO: 29)
10. Monkey blood     ISCSALLQNNIADAVACAKRVSDPQGIRAWVAWRNHCQNRDVSQYVKGCGV---------- (SEQ ID NO: 30)
11. Langur stomach   ISCSALLQNNIADAVACAKRVSDPQGIRAWVAWRNHCQNKDVSQYVKGCGV---------- (SEQ ID NO: 31)
    Invariant residues  C         CA                  W W     C                C
```

HUMAN SPERM SPECIFIC LYSOZYME-LIKE PROTEINS

The application is a US 371 filing of PCT/US01/01716 filed Jan. 19, 2000, which published as WO 01/053487, and which claims the benefit of U.S. 60/176,884, filed Jan. 19, 2000. This application also claims the benefit of U.S. 60/251,759, filed Dec. 7, 2000.

US GOVERNMENT RIGHTS

This invention was made with United States Government support under Grant No. HD U54 29099, awarded by the National Institutes of Health. The United States Government has certain rights in the invention.

FIELD OF THE INVENTION

The present invention is directed to directed to two novel, testis-specific proteins, designated C19 and C23. These proteins have been designated lysozyme paralogues due to their high degree of conservation of critical amino acids found in other lysozyme-C's.

BACKGROUND OF THE INVENTION

Lysozymes are hydrolases capable of lysing many bacteria. They cleave a beta-glycosidic bond between the C-1 of N-acetylmuramic acid and the C-4 of N-acetylglucosamine of the bacterial cell wall peptidoglycans (murein). Besides this muramidase activity they also display some chitinase (fungal cell wall component) activity. Lysozymes also are credited with antibacterial and antiviral capacities different from the bacteriolytic activity. For example, lysozymes have been demonstrated to have HIV 1 antiviral activity.

Lysozymes have been found in many biological tissues and secretions. Stomach lysozymes (cow, leaf-eating monkey) are even specialized to function at lower pH. There are two types of lysozymes found in the animal kingdom: C-type or chicken-type lysozymes represented by chicken egg white lysozyme, and G-type or goose type lysozymes represented by goose-egg white lysozyme. The C-type lysozymes are actually considered a superfamily including conventional lysozymes, calcium-binding lysozymes, and alpha-lactalbumins. All lysozymes have very similar tertiary structures, but vary in amino-acid composition.

Only one lysozyme has been identified and cloned from human tissues and body fluids. The gene coding for the human lysozyme is located on chromosome 12. A second lysozyme C gene was found on chromosome 17, but the corresponding protein has not been described (H. Nomiyama, J of Interferon and Cytokine Research 19: 227, 1999). Lysozyme C is a gene of 5856 bp and comprises four exons. The encoded protein is a secretory protein and comprises an 18 amino acid signal sequence and a mature protein of 130 residues. The mature protein contains four disulfide bonds between Cys 6—Cys 128, Cys 30—Cys 116, Cys 65—Cys 81, and Cys 77—Cys 95. This protein has been isolated from placenta, amniotic fluid, milk, tears, intestinal cells and leucocytes.

The present invention is directed to two human sperm proteins that have recently been isolated (C19 and C23) and appear to be lysozyme-C paralogues. These proteins are expressed specifically in sperm cell and are believed to function in the events relating to sperm/egg fusion and fertilization.

Definitions

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH$_2$— carbamate linkage (—CH$_2$OC(O)NR—), a phosphonate linkage, a —CH$_2$—sulfonamide (—CH$_2$—S(O)$_2$NR—) linkage, a urea (—NHC(O)NH—) linkage, a —CH$_2$— secondary amine linkage, or with an alkylated peptidyl linkage (—C(O)NR—) wherein R is C$_1$–C$_4$ alkyl;
2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or C$_1$–C$_4$ alkyl with the proviso that R and R$_1$ are not both hydrogen;
3. peptides wherein the C terminus is derivatized to —C(O)R$_2$ where R$_2$ is selected from the group consisting of C$_1$–C$_4$ alkoxy, and —NR$_3$R$_4$ where R$_3$ and R$_4$ are independently selected from the group consisting of hydrogen and C$_1$–C$_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is NMe; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for trytophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" are defined herein as exchanges within one of the following five groups:
I. Small aliphatic, nonpolar or slightly polar residues:
    Ala, Ser, Thr, Pro, Gly;
II. Polar, negatively charged residues and their amides:
    Asp, Asn, Glu, Gln;
III. Polar, positively charged residues:
    His, Arg, Lys;
IV. Large, aliphatic, nonpolar residues:
    Met Leu, Ile, Val, Cys
V. Large, aromatic residues:
    Phe, Tyr, Trp As used herein, the term "purified" and like terms relate to the isolation of a molecule or compound in a form that is substantially free of contaminants normally associated with the molecule or compound in a native or natural environment.

As used herein, the term "C19 polypeptide" and like terms refers to polypeptides comprising SEQ ID NO: 2 and biologically active fragments thereof (such as the mature form represented by SEQ ID NO: 8, for example) and the term "C23 polypeptide" and like terms refers to polypeptides comprising SEQ ID NO: 4 and biologically active fragments thereof (such as the mature form represented by SEQ ID NO: 9, for example).

As used herein, the term "biologically active fragment" or "bioactive fragment" of a C19 or C23 polypeptide encompasses natural or synthetic portions of SEQ ID NO: 2 or SEQ ID NO: 4, respectively, that are capable of specific binding to at least one of the natural ligands of the respective native polypeptide.

"Operably linked" refers to a juxtaposition wherein the components are configured so as to perform their usual function. Thus, control sequences or promoters operably linked to a coding sequence are capable of effecting the expression of the coding sequence.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

SUMMARY OF THE INVENTION

The present invention is directed to two lysozyme-like proteins (C19 and C23), nucleic acid sequences encoding those proteins, and antibodies generated against said proteins. Compositions comprising the native C19 or C23 peptides can be used in contraceptive vaccine formulations. Furthermore, antibodies generated against C19 and C23 can be used as diagnostic agents or can be formulated in compositions that are used to interfere with the binding of sperm cells to oocytes. In one embodiment, the present invention is directed to derivatives of the C19 and C23 proteins that have been modified to have lysozyme activity. These modified proteins can be used in any of the applications that currently use human lysozyme C, including antibacterial and antiviral formulations.

BRIEF DESCRIPTION OF THE DRAWINGS

FIG. 2 is a comparison of the mature C19 polypeptide (SEQ ID NO:8) with the mature lysozyme peptides of other species. The reference to SEQ ID NO:2 in the Figure next to the mature C19 polypeptide sequence is merely a reference to the SEQ ID NO of the full length C19 polypeptide which is a 215 amino acid residue polypeptide.

FIG. 3 is a comparison of the mature C23 polypeptide (SEQ ID NO:9) with the mature lysozyme peptides of other species. The reference to SEQ ID NO:4 in the Figure next to the mature C23 polypeptides sequence is merely a reference to the SEQ ID NO of the full length C23 polypeptide which is a 159 amino acid residue polypeptide.

DETAILED DESCRIPTION OF THE INVENTION

Figure 1A:
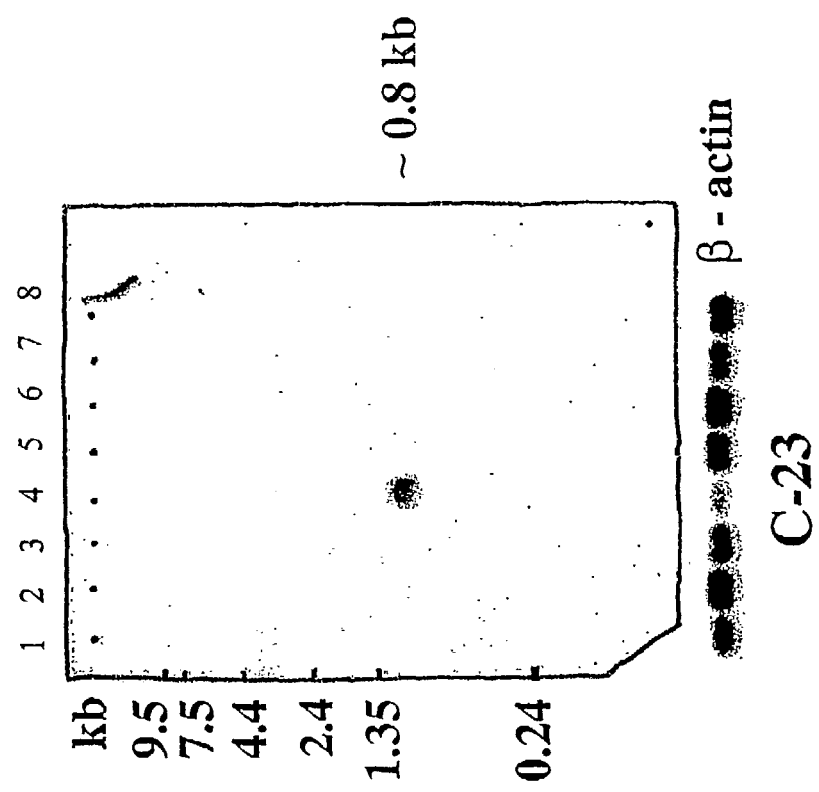
FIGS. 1A and 1B is a copy of a multiple tissue Northern Blot, wherein either C19 cDNA (FIG. 1A) or C23 cDNA (FIG. 1B) was radiolabeled with $p^{32}$ and hybridized to 2 ug poly-(A)+ mRNAs, revealing a 1 kb (FIG. 1A) or 0.8 kb (FIG. 1B) message only in testicular RNA. Size of molecular weight markers is indicated at left, lanes 1–8 contain poly-(A)+ mRNA isolated from spleen (lane 1) thymus (lane 2), prostate (lane 3), testis (lane 4), ovary (lane 5), small intestine (lane 6), colon (lane 7) and leucocyte (lane 8). The lower panel of FIGS. 1A and 1B shows the identical blot probed with β-actin cDNA as a positive control.

Two human sperm proteins have recently been isolated, C19 and C23, that appear to be lysozyme-C paralogues. These proteins are classified as lysozyme paralogues because of their high degree of conservation of critical amino acids linked in other lysozyme-C's. However they differ significantly from the known human lysozyme-C in nucleic acid and amino acid sequence, and their genes are located on different chromosomes. The new proteins C19 and C23 are approximately 15 kDa with pI's of 5.2 and 5.9, respectively. They possess sequence homology to the known human lysozyme-C; however, C19 and C23 are located on chromosome 17 and the X-chromosome, respectively, and thus these two genes represent new human lysozyme-like genes. The nucleic acid sequence and the deduced amino acid sequence of C19 are represented by SEQ ID NO: 1 and SEQ ID NO: 2, respectively, and nucleic acid sequence and the deduced amino acid sequence of C23 are represented by SEQ ID NO: 3, and SEQ ID NO: 4, respectively.

C19 and C23 each contain a signal peptide. The initial C19 polypeptide is synthesized as a 215 amino acid polypeptide (SEQ ID NO: 2) having a MW of 23.4 kDa and a pI of 8.0. The mature C19 peptide is 128 amino acids (SEQ ID NO: 8) and has a MW of about 14.6 kDa and pI of 5.0. The initial C23 polypeptide is synthesized as a 159 amino acid polypeptide (SEQ ID NO: 4) having a MW of 17.9 kDa and a pI of 5.9. The mature C23 peptide is 138 amino acids (SEQ ID NO: 9) and has a MW of about 15.7 kDa and pI of 5.9.

C19 and C23 have 48.8% sequence identity between one another and have 52% and 44% amino-acid sequence identity with the one known mature human lysozyme C, respectively, and 44% and 43% amino-acid sequence identity with the predicted lysozyme homologue on chromosome 17q11.2. C19 is most closely related to human lysozyme (52% sequence identity), whereas C23 is most closely related to chicken lysozyme (51% sequence identity).

The gene encoding C19 is located on Chromosome 17 and is 6012 bp in length. The C19 gene contains 5 exons (109, 309, 159, 79 and 164 bp, respectively) and 4 introns (3436, 1125, 443 and 188 bp, respectively). The gene encoding C23 is located on Chromosome Xp11.1 and is 1950 bp in length. The C23 gene contains 4 exons (169, 159, 79 and 181 bp, respectively) and 3 introns (429, 830, and 104 bp, respectively). Interestingly, exons 3 and 4 of C19 have a sequence identity with exons 2 and 3 of C23 greater than the overall sequence identity between the two complete proteins (i.e. greater than 48.8%) and exons 3 and 4 of C19 are identical in size to exons 2 and 3 of C23, respectively.

The expression of C19 and C23 is limited to the testes (see FIG. 1). To further characterize the expression of C19 and C23, antibodies were generated against C19 and C23. Those antibodies are specific for the target peptide and do not cross react with each other's respective lysozyme-like protein. C19 immunofluorescence and C19 and C23 EM localization experiments demonstrate that expression of the C19 and C23 proteins is localized in the sperm acrosome.

Recombinant C19 and C23 have been expressed in E. coli and in yeast. The proteins expressed in yeast were produced in a form that is secreted into the medium, and C19 was purified from the media and used in an assay to test for lysozyme activity. Secretion of the putatively processed forms of C19 and C23 (C23 was in crude form) as soluble proteins from Pichia pastoris revealed no lysozyme activity for C 19 and C23 using Micrococcus lysodeikticus as the lysozyme substrate. In particular, Micrococcus lysodeikticus was grown to confluence on a petri plate and the cells were contacted with 330 U of human lysozyme C (as a positive control), a reagent blank (as a negative control) and 1650 U of the purified soluble C19 protein (yrC19). Lysozyme activity was observed in the human lysozyme C portion (the positive control) as indicated by a zone of clearance about the introduce sample, but no activity was detected for yrC19. Although these compounds fail to exhibit lysozyme activity in the present assay, these compounds may still exhibit antibacterial/antiviral activity through an unknown mechanism.

Of all known lysozyme-C sequences (>75), 20 amino acid residues are invariant (see FIGS. 2 and 3). C19 contains all but two of those invariable amino acids (E35T, Y54N). The amino acid 35-E is considered a critical amino acid for catalytic function (i.e. cleaving the polysaccharide bond between N-acetylglucosamine and N-acetylmuramic acid). C23 contains all but one (D53E) of the 20 conserved amino acids. The amino acid 53-D is considered a critical amino acid for catalytic function; however, g-type lysozymes do not have a D in the corresponding position. Homologous genes of C19 and C23 have also been isolated by applicants from other mammalian species (for example, mice), that contain similar mutations in the catalytic residues of these genes.

In accordance with one embodiment of the present invention, modified versions of the C19 and C23 proteins are provided wherein the 35-T of C19 is converted to 35-E (SEQ ID NO: 5) and the 53-E of C23 is converted to 53-D (SEQ ID NO: 6). It is anticipated that when these single amino acid substitutions are made in each lysozyme-like protein, the modified proteins will exhibit lysozyme activity and thus can be used as alternative compounds in all applications currently utilizing known human lysozyme-C. Furthermore, in one embodiment a modified version of C19 is prepared wherein the 35-T is converted to 35-E and 54-N is converted to 54-Y (SEQ ID NO: 7). This modified version of C19 is also expected to have lysozyme activity.

The C19 and C23 native polypeptides when modified to have lysozyme activity can be used in any of the applications described in U.S. Pat. No. 4,945,051, U.S. Pat. No. 5,585, 257, U.S. Pat. No. 5,618,712 and WO 9924589 (DE19749973), the disclosures of which are expressly incorporated herein. The novel lysozymes of the present invention can also be used as the active agent in antibacterial wound dressings, dental plaque preventing formulations, anti-inflammatory throat lozenges, anti-acne compositions, sprays for controlling dry mouth condition and as food additives to prevent spoilage. It has also been reported that lysozyme may be effective against HIV (Lee-Huang. S., PNAS 96:2678, 1999).

In one embodiment, a polypeptide comprising an amino acid sequence selected from the group consisting of SEQ ID NO: 8, SEQ ID NO: 9, SEQ ID NO: 10, and SEQ ID NO: 11 is used as the active agent in an antibacterial and antiviral composition. In one preferred embodiment, a polypeptide comprising an amino acid sequence of SEQ ID NO: 10 or SEQ ID NO: 11 is used as an antibacterial and antiviral agent. The lysozyme proteins of the present invention can also be combined with standard antibacterial and antiviral agents to enhance the efficacy of those agents. In accordance with one embodiment, a composition comprising an amino acid sequence selected from the group consisting of SEQ ID NO: 8, SEQ ID NO: 9, SEQ ID NO: 10, and SEQ ID NO: 11 is used as an antibacterial/antiviral additives to intravaginal gels or foams to reduce the risk of sexually transmitted diseases.

In another embodiment, compositions comprising the native C19 or C23 polypeptides or fragments thereof are used as contraceptive agents. In particular, the unmodified C19 and C23 proteins are anticipated to have sperm specific functions that can be the basis of a contraceptive vaccine, designed to prevent capacitation/fertilization. For example in accordance with one embodiment the C19 or C23 polypeptides or fragments thereof, are used as components of a contraceptive vaccine.

In one aspect of the invention, C19 and C23 polypeptides (either separately or in combination) are delivered to a subject to elicit an active immune response. The vaccine acts as a temporary and reversible antagonist of the function of the egg surface proteins of the invention. For example, such vaccines could be used for active immunization of a subject, to raise an antibody response to temporarily block the sperm's access to the egg plasma antigen. In one aspect of the invention, an antigen could be administered at a certain period of the month, for example during ovulation of a female subject to block fertilization.

In another aspect of the invention, C19 and C23 polypeptides (either separately or in combination) are used as vaccines for permanent sterilization of a subject. Such vaccines can be used to elicit a T-cell mediated attack on the eggs, having an othoritic effect, useful as a method for irreversible sterilization. Methods for generating T-cell specific responses, such as adoptive immunotherapy, are well known in the art (see, for example, Vaccine Design, Michael F. Powell and Mark J. Newman Eds., Plenum Press, New York, 1995, pp 847–867). Such techniques may be particular useful for vetinary contraceptive or sterilization purposes, where a single dose vaccination may be desirable.

In one embodiment, the present invention is directed to a purified polypeptide comprising the amino acid sequence of SEQ ID NO: 2, or an amino acid sequence that differs from SEQ ID NO: 2 by one or more conservative amino acid substitutions. More preferably, the purified polypeptide comprises an amino acid sequence that differs from SEQ ID NO: 2 by 10 or less conservative amino acid substitutions. Alternatively, the polypeptide may comprise an amino acid sequence that differs from SEQ ID NO: 2 by 1 to 3 alterations, wherein the alterations are independently selected from a single amino acid deletion, insertion or substitution.

Alternatively, one embodiment of the present invention is directed to a purified polypeptide comprising the amino acid sequence of SEQ ID NO: 4, or an amino acid sequence that differs from SEQ ID NO: 4 by one or more conservative amino acid substitutions. More preferably, the purified polypeptide comprises an amino acid sequence that differs from SEQ ID NO: 4 by 10 or less conservative amino acid substitutions. Alternatively, the polypeptide may comprise an amino acid sequence that differs from SEQ ID NO: 4 by 1 to 3 alterations, wherein the alterations are independently selected from a single amino acid deletion, insertion or substitution.

Another embodiment of the present invention encompasses polypeptides comprising an amino acid sequence selected from the group consisting of SEQ ID NO: 5, SEQ ID NO: 6, SEQ ID NO: 7, SEQ ID NO: 8, SEQ ID NO: 9 and amino acid sequences that differs from SEQ ID NO: 5, SEQ ID NO: 6, SEQ ID NO: 7, SEQ ID NO: 8 or SEQ ID NO: 9 by 10 or less conservative amino acid substitutions. The present invention also encompasses fragments of SEQ ID NO: 2 and SEQ ID NO: 4, wherein the peptide fragment is at least ten amino acids in length and comprises ten contiguous amino acids that are identical in sequence to an ten contiguous amino portion of SEQ ID NO: 2 or SEQ ID NO: 4.

In one embodiment, the present invention provides methods of screening for agents, small molecules, or proteins that interact with polypeptides of SEQ ID NO: 2 or SEQ ID NO: 4. The invention encompasses both in vivo and in vitro assays to screen small molecules, compounds, recombinant proteins, peptides, nucleic acids, antibodies etc. which bind to or modulate the activity of C19 or C23 and are thus useful as therapeutics or diagnostic markers for fertility.

For example, the C19 or C23 polypeptide, or a bioactive fragment thereof, can be used to isolate ligands that bind to the respective native polypeptide under physiological conditions. The method comprises the steps of contacting the C19 or C23 polypeptide with a mixture of compounds under physiological conditions, removing unbound and non-specifically bound material, and isolating the compounds that remain bound to the C19 or C23 polypeptide. Typically, the C19 or C23 polypeptide will be bound to a solid support using standard techniques to allow rapid screening compounds. The solid support can be selected from any surface that has been used to immobilize biological compounds and includes but is not limited to polystyrene, agarose, silica or nitrocellulose. In one embodiment the solid surface comprises functionalized silica or agarose beads. Screening for such compounds can be accomplished using libraries of pharmaceutical agents and standard techniques known to the skilled practitioner.

In accordance with one embodiment the C19 and C28 polypeptides and peptide fragments are used to isolate oocyte proteins that bind to C19 and C28. The procedures for recovering oocyte proteins and screening for ligands that bind to C19 and C23 are well known to those skilled in the art. In one embodiment the C19 or C23 polypeptide is immobilized to a solid support and the proteins are contacted with a solution/suspension of oocyte proteins under conditions that allow binding. Unbound and non-specific bound materials are then washed from the solid support and the remaining bound materials are recovered and analyzed (by microsequencing, for example). Microsequencing of the recovered proteins will allow for the design of nucleic acid probes and primers for the identification and cloning of the corresponding genes that encode the recovered proteins.

The present invention also encompasses nucleic acid sequences that encode the C19 and C23 polypeptides, and bioactive fragments and derivatives thereof. In particular the present invention is directed to nucleic acid sequences comprising the sequence of SEQ ID NO: 1, or SEQ ID NO: 3, or fragments thereof. In one embodiment, purified nucleic acids comprising at least 20 contiguous nucleotides (i.e., a hybridizable portion) that are identical to any 20 contiguous nucleotides of SEQ ID NO: 1 or SEQ ID NO: 3 are provided. In other embodiments, the nucleic acids comprises at least 25 (contiguous) nucleotides, 50 nucleotides, 100 nucleotides, or 200 nucleotides of SEQ ID NO: 1 or SEQ ID NO: 3.

One embodiment of the present invention includes nucleic acids that hybridize (under conditions defined herein) to all or a portion of the nucleotide sequence represented by SEQ ID NO: 1 or its complement. Alternatively, the present invention also includes nucleic acids that hybridize (under conditions defined herein) to all or a portion of the nucleotide sequence represented by SEQ ID NO: 3 or its complement. The hybridizing portion of the hybridizing nucleic acids is typically at least 15 (e.g., 20, 25, 30, or 50) nucleotides in length. Hybridizing nucleic acids of the type described herein can be used, for example, as a cloning probe, a primer (e.g., a PCR primer), or a diagnostic probe. The DNA sequence of SEQ ID NO: 1, SEQ ID NO: 3, or fragments thereof, can be used as probes to detect homologous genes from other vertebrate species.

Nucleic acid duplex or hybrid stability is expressed as the melting temperature or Tm, which is the temperature at which a nucleic acid duplex dissociates into its component single stranded DNAs. This melting temperature is used to define the required stringency conditions. Typically a 1% mismatch results in a 1° C. decrease in the Tm, and the temperature of the final wash in the hybridization reaction is reduced accordingly (for example, if two sequences having >95% identity, the final wash temperature is decreased from the Tm by 5° C.). In practice, the change in Tm can be between 0.5° C. and 1.5° C. per 1% mismatch.

The present invention is directed to the nucleic acid sequence of SEQ ID NO: 1 and SEQ ID NO: 3, and nucleic acid sequences that hybridize to those sequences (or fragments thereof) under stringent or highly stringent conditions. In accordance with the present invention highly stringent conditions are defined as conducting the hybridization and wash conditions at no lower than −5° C. Tm. Stringent conditions are defined as involve hybridizing at 68° C. in 5×SSC/5× Denhardt's solution/1.0% SDS, and washing in 0.2×SSC/0.1% SDS at 68° C. Moderately stringent conditions include hybridizing at 68° C. in 5×SSC/5× Denhardt's solution/1.0% SDS and washing in 3×SSC/0.1% SDS at 42° C. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In another embodiment of the present invention, nucleic acid sequences encoding the C19 or C23 polypeptides can be inserted into expression vectors and used to transfect cells to enhance the expression of those proteins on the target cells. In accordance with one embodiment, nucleic acid sequences encoding C19 or C23, or a fragment or a derivative thereof, are inserted into a eukaryotic expression vector in a manner that operably links the gene sequences to the appropriate regulatory sequences, and recombinant C19 or recombinant C23 is expressed in a eukaryotic host cell. Suitable eukaryotic host cells and vectors are known to those skilled in the art. In particular, nucleic acid sequences encoding C19 or C23 may be added to a cell or cells in vitro or in vivo using delivery mechanisms such as liposomes, viral based vectors, or microinjection. Accordingly, one aspect of the present invention is directed to transgenic cell lines that contain recombinant genes that express C19 or C23.

The present invention also encompasses antibodies, including anti-idiotypic antibodies, antagonists and agonists, as well as compounds or nucleotide constructs that inhibit expression of the C19 and C23 genes (transcription factor inhibitors, antisense and ribosome molecules, or gene or regulatory sequence replacement constructs), or promote expression of C19 and C23 (e.g., expression constructs in which C19 or C23 coding sequences are operatively associated with expression control elements such as promoters, promoter/enhancers, etc.). Antagonists of C19 and/or C23 function can be used to interfere with the capacitation of vertebrate sperm and fertilization of an ovum, and thus used as contraceptive agents. Furthermore, antibodies against the C19 or C23 protein can be used for the diagnosis of conditions or diseases characterized by expression or overexpression of C19 or C23, or in assays to monitor patients being treated with C19 or C23 agonists, antagonists or inhibitors.

In accordance with one embodiment, antibodies are provided that specifically bind to C19 or C23. In particular, a C19 or C23 polypeptide, fragments thereof, or other derivatives, or analogs thereof, may be used as an immunogen to generate antibodies which immunospecifically bind such an immunogen. In accordance with one embodiment of the preset invention an antigenic compound is provided for generating antibodies, wherein the compound comprises an amino acid sequence selected from the group consisting of SEQ ID NO: 2, SEQ ID NO: 4, SEQ ID NO: 5, SEQ ID NO: 6, SEQ ID NO: 7, SEQ ID NO: 8 and SEQ ID NO: 9. The antibodies generated can be formulated with standard carriers and optionally labeled to prepare therapeutic or diagnostic compositions. Antibodies to C19 or C23 may be generated using methods that are well known in the art.

In one embodiment, rabbit polyclonal antibodies to an epitope of C19 or C23, is obtained. For the production of antibody, various host animals, including but not limited to rabbits, mice, rats, etc can be immunized by injection with a C19 or C23 peptide. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward an egg surface protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for epitopes of C19 or C23 together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce egg surface protein-specific single chain antibodies. An additional embodiment of the invention utilizes the techniques described for the construction of Fab expression libraries (Fuse et al., 1989, Science 246:1275–1281) to allow rapid and easy identification of monoclonal Fab fragments with the desired specificity for egg surface proteins, derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). The foregoing antibodies can be used in methods known in the art relating to the localization and activity of the C19 or C23 proteins of the invention, e.g., for imaging these proteins, measuring levels thereof in appropriate physiological samples, in diagnostic methods, etc.

Antibodies generated in accordance with the present invention may include, but are not limited to, polyclonal, monoclonal, chimeric (i.e "humanized" antibodies), single chain (recombinant), Fab fragments, and fragments produced by a Fab expression library. These antibodies can be used as diagnostic agents for the diagnosis of conditions or diseases characterized by expression or overexpression of C19 or C23, or in assays to monitor patients being treated with C19 or C23 receptor agonists, antagonists or inhibitors. The antibodies useful for diagnostic purposes may be prepared in the same manner as those described above for therapeutics. The antibodies may be used with or without modification, and may be labeled by joining them, either covalently or non-covalently, with a reporter molecule.

In accordance with one embodiment an antibody is provided that specifically binds to a polypeptide selected from the group consisting of SEQ ID NO: 2, SEQ ID NO: 4, SEQ ID NO: 5, SEQ ID NO: 6, SEQ ID NO: 7, SEQ ID NO: 8 and SEQ ID NO: 9. In one preferred embodiment the antibody is a monoclonal antibody.

In one embodiment antibodies against the C19 and/or C23 proteins are used as contraceptive agents that prevent the binding of sperm cells to eggs. An experiment was conducted to determine if the antibodies against C19 and C23 could interfere human sperm's ability to bind to eggs (See Example 2). The assay was conducted in vitro using human sperm and hamster eggs. C19 and C23 are on the acrosome membrane and are only exposed upon permeablization of the acrosome. Only approximately ⅓ of sperm undergo acrosome reaction in vitro. As seen in Example 2, antibodies against C19 significantly interfered with sperm cells ability to bind to hamster eggs while no effect was observed for the antibody generated against C23. These results suggest that a unique receptor for the C19 protein may exist on mammalian eggs, and this receptor itself could serve as a target for contraceptive agents.

The present invention also encompasses compositions that can be placed in contact with sperm cells to inhibit the function of the C19 and C23 protein (i.e. either by inhibiting the expression of the C19 and C23 proteins or by interfering with the protein's function). In particular the compositions may comprise peptide fragments of C19 or C23, or analogs thereof that are taken up by the sperm cells and compete for binding with C19 and C23's natural ligands. Such inhibitory peptides can be modified to include fatty acid side chains to assist the peptides in penetrating the sperm cell membrane. Compositions comprising a C19 or C23 inhibitory agent can be used to modulate fertility of an individual, and in one embodiment, the inhibitory agents function as a male contraceptive pharmaceutical. In accordance with one embodiment a composition is provided that comprises an eight to fifteen amino acid sequence that is identical to an eight to fifteen contiguous amino acid sequence of SEQ ID NO: 2 or SEQ ID NO: 4 and a pharmaceutically acceptable carrier.

EXAMPLE 1

Isolation of the C19 and C23 Proteins

Materials and Methods

Solubilization and Electrophoresis of Human Spermatozoal Proteins

Preparation of semen specimens and solubilization of sperm proteins were performed as previously described (Naaby-Hansen et al, 1997a.) For analytical two-dimensional electrophoresis the detergent/urea extracted proteins were separated by isoelectric focusing (IEF) in acrylamide tube gels prior to second dimensional gel electrophoresis (SDS-PAGE), which was performed in a Protean II xi Multi-Cell apparatus (Bio-Rad, Richmond, Calif.) or on large format (23×23 cm) gels (Investigator 2-D Electrophoresis System, ESA) which were also employed for preparative 2D gel electrophoresis. Electrotransfer to nitrocellulose membranes and subsequent visualizing of the proteins by gold staining was accomplished as previously described (Naaby-Hansen et al, 1997) while electrotransfer to PVDF membranes (0.2 mm pore size, Pierce) was carried out as described by Henzel et al. (1993) using the transfer buffer composition of Matsudaira (1987) (10 mM 3-[cyclohexylamino]-1-propanesulfonic acid, 10% methanol, pH-11). The immobilized proteins were visualized by staining in a solution containing 0.1% Commassie R250, 40% methanol and 0.1% acetic acid for one minute, followed by destaining in a solution of 10% acetic acid and 50% methanol for 3×3 minutes.

Generation of Antiserum Against Gel Purified C19 and C23

The 86 kDa Coomassie-stained protein spot was cored from three 1.5 mm thick 2-D SDS-PAGE gels of human sperm extracts. The gel cylinders were minced into a slurry in 1 ml of PBS and emulsified with an equal volume of complete Freunds adjuvant. Six hundred ul of this emulsion was intradermally injected into a New Zealand white rabbit, followed by two monthly subcutaneous booster injections of similarly-prepared antigen with incomplete Freunds adjuvant. Serum was collected 10 days after each booster injection.

Microsequencing of the C19 and C23 Proteins

The C19 and C23 stained protein spots were cored from a 1.5 mm thick 2D SDS-polyacrylamide gel and fragmented into smaller pieces. The proteins were destained in methanol, reduced in 10 mM dithiothreitol and alkylated in 50 mM iodoacetamide in 0.1 M ammonium bicarbonate. After removing the reagents, the gel pieces were incubated with 12.5 ng/ml trypsin in 50 MM ammonium bicarbonate overnight at 37° C. Peptides were extracted from the gel pieces in 50% acetonitrile in 5% formic acid and microsequenced by tandem mass spectrometry and by Edman degradation at the Biomolecular Research Facility of the University of Virginia. Differentiation of leucine and isoleucine in the sequences were determined by Edman sequencing of HPLC isolated peptides. A degenerate deoxyinosine containing primers were used to isolate the C19 and C23 cDNA clones based on the microsequencing data and using PCR technology.

Northern and Dot Blot Analyses

Figure 1B:
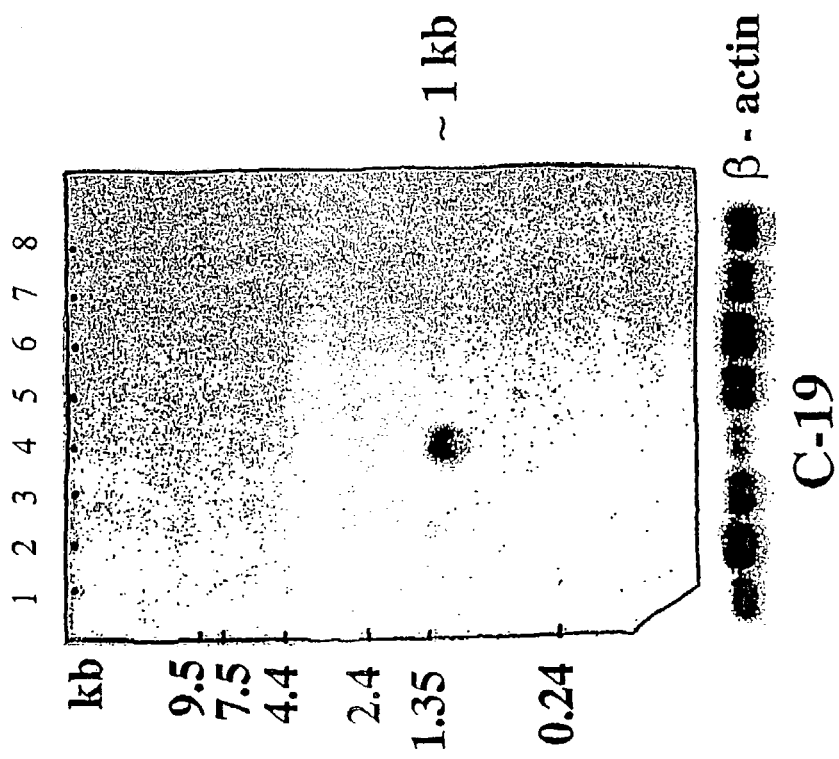

A Northern blot containing 2 mg of poly(A)$^+$ RNA from eight selected human tissues was obtained from Clontech. The Northern blot was probed with a $^{32}$P labeled C19 cDNA (FIG. 1A) or $^{32}$P-labeled C23 cDNA (FIG. 1B). Probes were prepared by random oligonucleotide prime labeling (Feinberg and Vogelstein, 1983). Hybridization was performed in ExpressHyb solution (Clontech) at 68° C. for 1 h followed by three washes in 2×SSC, 0.05% SDS at room temperature and two washes in 0.1×SSC, 0.1% SDS for 20 min at 50° C.

A normalized RNA dot blot containing 89 to 514 ng of mRNA from 50 different human tissues was obtained from Clontech and probed with $^{32}$P-labeled C19 EDNA or $^{32}$P-labeled C23 cDNA. The normalized (100–500 ng) poly-(A)+ mRNAs present on the grid were isolated from various tissue sources including: whole brain, amygdala, caudate nucleus, cerebellum, cerebral cortex, frontal lobe, hippocampus, medulla oblongata, occipitallobe, putamen, substantia nigra, temporal lobe, thalamus, subthalmic nucleus, spinal chord, heart, aorta, skeletal muscle, colon, bladder, uterus, prostate, stomach, testis, ovary, pancreas, pituitary gland, adrenal gland, thyroid gland, salivary gland, mammary gland, kidney, liver, small intestine, spleen, thymus, peripheral leukocyte, lymph node, bone marrow, appendix, lung, trachea, placenta, fetal brain, fetal heart, fetal kidney, fetal liver, fetal spleen, fetal thymus, fetal lung, and 100 ng total yeast RNA, 100 ng yeast tRNA, 100 ng E. coli rRNA, 100 ng E. coli DNA, 100 ng poly r(A), 100 ng Cot 1 human DNA, 100 ng human DNA, 500 ng human DNA. The blot was hybridized in ExpressHyb solution (Clontech) containing salmon sperm DNA and human placental Cot-1 DNA overnight at 65° C. The blot was then washed three times in 2×SSC, 1% SDS at 65° C. followed by two additional washes in 0.1×SSC, 0.5% SDS at 55° C. before exposing the filter to X-Ray film. Hybridization was only detected in the testis RNA dot.

EXAMPLE 2

Human Sperm Binding and Fusion Assay Using Zona-Free Hamster Eggs

Sperm Preparation:

Motile sperm were harvested by the swim up method of Bronson and Fusi (1990). Briefly, a 500 ml sperm sample underlaid in 2 ml of BWW media containing 5 mg/ml HSA. Sperm were allowed to swim up for 1.5–2 h. Swimup sperm were collected and 8 ml of BWW+5 mg/ml HSA was added.

The composition was spin at 600×g for 8 min at RT, the supernatant was removed and 8 ml of media was added to the pellet. The resuspended pellet was spun at 600×g for 8 min at RT. The supernatant was removed and 50 ml of BWW containing 30 mg/ml HSA was added to the pellet. Total sperm cells were counted and then incubated overnight in BWW+30 mg/ml HSA at a concentration of 20×10$^6$ sperm/ml.

Egg Collection:

Female hamsters received i.p. injections of 30 IU PMSG followed by 30 IU of hCG 72 h later. 14–16 h following hCG injection, hamsters were sacrificed and oviducts are collected in BWW media containing 5 mg/ml HSA. Cumulus cells were removed with 1 mg/ml hyaluronidase, the eggs were washed and zona pellucidae removed with 1 mg/ml trypsin. The eggs were then thoroughly washed and allowed to rest in the incubator.

Sperm/Antibody Incubation:

Sperm was diluted to 20×10$^6$ sperm/ml and incubated with appropriate dilutions of pre-immune or immune sera (initially a 1:10 and 1:50 dilution of sera is tested) in paraffin oil covered microdrops for 1 h.

Hamster eggs were added to the drops containing the sperm+antibody. The gametes were then co-incubated for 3 h.

Assessment of Binding and Fusion:

Eggs were washed free of unbound and loosely bound sperm by serial passage through 5 (50 ml) wash drops. The same pipet is used for all eggs washed in an individual experiment. Eggs are then stained by short-term (5–15 s) exposure to 1 mM acridine orange-3% DMSO in BSA/BWW (30 mg/ml), washed through 4 (50 ml) wash drops and mounted under 22×22 mm coverslips. Under UV illumination, unexpanded head s of oolemma-adherant sperm were counted and sperm that had penetrated the ooplasm exhibited expanded green heads. All experiments were repeated 3 times

| Results |
|---|
| 1:10 dilution of C19 Antibody |

| | Number of sperm bound per egg | | |
|---|---|---|---|
| Pre Immune | 38.2 | Immune | 21.8 |
| | P value = 7.78 × 10$^6$ | | |
| | Number of sperm fused per egg | | |
| Pre Immune | 3.2 | Immune | 2.9 |
| | P value = 0.6 | | |

| 1:10 dilution of C23 Antibody |
|---|

| | Number of sperm bound per egg | | |
|---|---|---|---|
| Pre Immune | 28.7 | Immnune | 27.4 |
| | P value = 0.79 | | |
| | Number of sperm fused per egg | | |
| Pre Immune | 1.8 | Immune | 1.6 |
| | P value = 0.71 | | |

We claim:

1. A method for inhibiting sperm binding to an oocyte in vitro, said method comprising contacting the sperm with an antibody directed against the polypeptide of SEQ ID NO: 2 prior to binding of said sperm with said oocyte, wherein said antibody inhibits sperm binding to the oocyte.

2. The method of claim 1 wherein said antibody is a polyclonal antibody or a monoclonal antibody.

* * * * *

SEQUENCE LISTING

```
<160> NUMBER OF SEQ ID NOS: 31

<210> SEQ ID NO 1
<211> LENGTH: 820
<212> TYPE: DNA
<213> ORGANISM: Homo sapiens

<400> SEQUENCE: 1
gccctggcaa ggttgtgggg gacatcttga gctgaagcag ggttttgagc cactgctgct    60
gctgccattg tcaccatggt ctcagctctg cggggagcac ccctgatcag ggtgcactca   120
agccctgttt cttctccttc tgtgagtgga ccacggaggc tggtgagctg cctgtcatcc   180
caaagctcag ctctgagcca gagtggtggt ggctccacct ctgccgccgg catagaagcc   240
aggagcaggg ctctcagaag gcggtggtgc ccagctggga tcatgttgtt ggccctggtc   300
tgtctgctca gctgcctgct accctccagt gaggccaagc tctacggtcg ttgtgaactg   360
gccagagtgc tacatgactt cgggctggac ggataccggg gatacagcct ggctgactgg   420
gtctgccttg cttatttcac aagcggtttc aacgcagctg ctttggacta cgaggctgat   480
gggagcaccg acaacgggat cttccagatc aacagccgga ggtggtgcag caacctcacc   540
ccgaacgtcc ccaacgtgtg ccggatgtac tgctcagatt tgttgaatcc taatctcaag   600
gataccgtta tctgtgccat gaagataacc caagagcctc agggtctggg ttactgggag   660
gcctggaggc atcactgcca gggaaaagac ctcactgaat gggtggatgg ctgtgacttc   720
taggatggac ggaaccatgc acagcaggct gggaaatgtg gtttggttcc tgacctaggc   780
ttgggaagac aagccagcga ataaaggatg gttgaacgtt                          820
```

<210> SEQ ID NO 2
<211> LENGTH: 215
<212> TYPE: PRT
<213> ORGANISM: Homo sapiens

<400> SEQUENCE: 2

```
Met Val Ser Ala Leu Arg Gly Ala Pro Leu Ile Arg Val His Ser Ser
  1               5                  10                  15

Pro Val Ser Ser Pro Ser Val Ser Gly Pro Arg Arg Leu Val Ser Cys
             20                  25                  30

Leu Ser Ser Gln Ser Ser Ala Leu Ser Gln Ser Gly Gly Gly Ser Thr
         35                  40                  45

Ser Ala Ala Gly Ile Glu Ala Arg Ser Arg Ala Leu Arg Arg Arg Trp
 50                  55                  60

Cys Pro Ala Gly Ile Met Leu Leu Ala Leu Val Cys Leu Leu Ser Cys
 65                  70                  75                  80

Leu Leu Pro Ser Ser Glu Ala Lys Leu Tyr Gly Arg Cys Glu Leu Ala
                 85                  90                  95

Arg Val Leu His Asp Phe Gly Leu Asp Gly Tyr Arg Gly Tyr Ser Leu
            100                 105                 110

Ala Asp Trp Val Cys Leu Ala Tyr Phe Thr Ser Gly Phe Asn Ala Ala
        115                 120                 125

Ala Leu Asp Tyr Glu Ala Asp Gly Ser Thr Asp Asn Gly Ile Phe Gln
    130                 135                 140

Ile Asn Ser Arg Arg Trp Cys Ser Asn Leu Thr Pro Asn Val Pro Asn
145                 150                 155                 160

Val Cys Arg Met Tyr Cys Ser Asp Leu Leu Asn Pro Asn Leu Lys Asp
                165                 170                 175

Thr Val Ile Cys Ala Met Lys Ile Thr Gln Glu Pro Gln Gly Leu Gly
            180                 185                 190

Tyr Trp Glu Ala Trp Arg His His Cys Gln Gly Lys Asp Leu Thr Glu
        195                 200                 205

Trp Val Asp Gly Cys Asp Phe
    210                 215
```

<210> SEQ ID NO 3
<211> LENGTH: 588
<212> TYPE: DNA
<213> ORGANISM: Homo sapiens

<400> SEQUENCE: 3

| | | |
|---|---|---|
| ctgggagggc ttacaggtgc cataatgaag gcctggggca ctgtggtagt gaccttggcc | 60 |
| acgctgatgg ttgtcactgt ggatgccaag atctatgaac gctgcgagct ggcggcaaga | 120 |
| ctggagagag cagggctgaa cggctacaag ggctacggcg ttggagactg gctgcatg | 180 |
| gctcattatg agagtggctt tgacaccgcc ttcgtggacc acaatcctga tgcagcagt | 240 |
| gaatatggca ttttccaact gaattctgcc tggtggtgtg acaatggcat tacacccacc | 300 |
| aagaacctct gccacatgga ttgtcatgac ctgctcaatc gccatattct ggatgacatc | 360 |
| aggtgtgcca agcagattgt gtcctcacag aatgggcttt ctgcctggac ttcttggagg | 420 |
| ctacactgtt ctggccatga tttatctgaa tggctcaagg ggtgtgatat gcatgtgaaa | 480 |
| attgatccaa aaattcatcc atgactcaga ttcgaagaga cagattttat cttcctttca | 540 |
| tttctttctc ttgtgcattt aataaggat ggtatctata aacaatgc | 588 |

-continued

```
<210> SEQ ID NO 4
<211> LENGTH: 159
<212> TYPE: PRT
<213> ORGANISM: Homo sapiens

<400> SEQUENCE: 4

Met Lys Ala Trp Gly Thr Val Val Thr Leu Ala Thr Leu Met Val
 1               5                  10                  15

Val Thr Val Asp Ala Lys Ile Tyr Glu Arg Cys Glu Leu Ala Ala Arg
                20                  25                  30

Leu Glu Arg Ala Gly Leu Asn Gly Tyr Lys Gly Tyr Gly Val Gly Asp
            35                  40                  45

Trp Leu Cys Met Ala His Tyr Glu Ser Gly Phe Asp Thr Ala Phe Val
    50                  55                  60

Asp His Asn Pro Asp Gly Ser Ser Glu Tyr Gly Ile Phe Gln Leu Asn
 65                  70                  75                  80

Ser Ala Trp Trp Cys Asp Asn Gly Ile Thr Pro Thr Lys Asn Leu Cys
                85                  90                  95

His Met Asp Cys His Asp Leu Leu Asn Arg His Ile Leu Asp Asp Ile
            100                 105                 110

Arg Cys Ala Lys Gln Ile Val Ser Ser Gln Asn Gly Leu Ser Ala Trp
        115                 120                 125

Thr Ser Trp Arg Leu His Cys Ser Gly His Asp Leu Ser Glu Trp Leu
    130                 135                 140

Lys Gly Cys Asp Met His Val Lys Ile Asp Pro Lys Ile His Pro
145                 150                 155

<210> SEQ ID NO 5
<211> LENGTH: 215
<212> TYPE: PRT
<213> ORGANISM: Homo sapiens

<400> SEQUENCE: 5

Met Val Ser Ala Leu Arg Gly Ala Pro Leu Ile Arg Val His Ser Ser
 1               5                  10                  15

Pro Val Ser Ser Pro Ser Val Ser Gly Pro Arg Arg Leu Val Ser Cys
                20                  25                  30

Leu Ser Ser Gln Ser Ser Ala Leu Ser Gln Ser Gly Gly Gly Ser Thr
            35                  40                  45

Ser Ala Ala Gly Ile Glu Ala Arg Ser Arg Ala Leu Arg Arg Arg Trp
    50                  55                  60

Cys Pro Ala Gly Ile Met Leu Leu Ala Leu Val Cys Leu Leu Ser Cys
 65                  70                  75                  80

Leu Leu Pro Ser Ser Glu Ala Lys Leu Tyr Gly Arg Cys Glu Leu Ala
                85                  90                  95

Arg Val Leu His Asp Phe Gly Leu Asp Gly Tyr Arg Gly Tyr Ser Leu
            100                 105                 110

Ala Asp Trp Val Cys Leu Ala Tyr Phe Glu Ser Gly Phe Asn Ala Ala
        115                 120                 125

Ala Leu Asp Tyr Glu Ala Asp Gly Ser Thr Asp Asn Gly Ile Phe Gln
    130                 135                 140

Ile Asn Ser Arg Arg Trp Cys Ser Asn Leu Thr Pro Asn Val Pro Asn
145                 150                 155                 160

Val Cys Arg Met Tyr Cys Ser Asp Leu Leu Asn Pro Asn Leu Lys Asp
                165                 170                 175
```

```
Thr Val Ile Cys Ala Met Lys Ile Thr Gln Glu Pro Gln Gly Leu Gly
            180                 185                 190

Tyr Trp Glu Ala Trp Arg His His Cys Gln Gly Lys Asp Leu Thr Glu
        195                 200                 205

Trp Val Asp Gly Cys Asp Phe
    210                 215

<210> SEQ ID NO 6
<211> LENGTH: 159
<212> TYPE: PRT
<213> ORGANISM: Homo sapiens

<400> SEQUENCE: 6

Met Lys Ala Trp Gly Thr Val Val Thr Leu Ala Thr Leu Met Val
 1               5                  10                  15

Val Thr Val Asp Ala Lys Ile Tyr Glu Arg Cys Glu Leu Ala Ala Arg
                20                  25                  30

Leu Glu Arg Ala Gly Leu Asn Gly Tyr Lys Gly Tyr Gly Val Gly Asp
            35                  40                  45

Trp Leu Cys Met Ala His Tyr Glu Ser Gly Phe Asp Thr Ala Phe Val
50                  55                  60

Asp His Asn Pro Asp Gly Ser Ser Asp Tyr Gly Ile Phe Gln Leu Asn
65                  70                  75                  80

Ser Ala Trp Trp Cys Asp Asn Gly Ile Thr Pro Lys Asn Leu Cys
                85                  90                  95

His Met Asp Cys His Asp Leu Leu Asn Arg His Ile Leu Asp Asp Ile
            100                 105                 110

Arg Cys Ala Lys Gln Ile Val Ser Ser Gln Asn Gly Leu Ser Ala Trp
        115                 120                 125

Thr Ser Trp Arg Leu His Cys Ser Gly His Asp Leu Ser Glu Trp Leu
    130                 135                 140

Lys Gly Cys Asp Met His Val Lys Ile Asp Pro Lys Ile His Pro
145                 150                 155

<210> SEQ ID NO 7
<211> LENGTH: 215
<212> TYPE: PRT
<213> ORGANISM: Homo sapiens

<400> SEQUENCE: 7

Met Val Ser Ala Leu Arg Gly Ala Pro Leu Ile Arg Val His Ser Ser
 1               5                  10                  15

Pro Val Ser Ser Pro Ser Val Ser Gly Pro Arg Arg Leu Val Ser Cys
                20                  25                  30

Leu Ser Ser Gln Ser Ser Ala Leu Ser Gln Ser Gly Gly Ser Thr
            35                  40                  45

Ser Ala Ala Gly Ile Glu Ala Arg Ser Arg Ala Leu Arg Arg Arg Trp
50                  55                  60

Cys Pro Ala Gly Ile Met Leu Leu Ala Leu Val Cys Leu Leu Ser Cys
65                  70                  75                  80

Leu Leu Pro Ser Ser Glu Ala Lys Leu Tyr Gly Arg Cys Glu Leu Ala
                85                  90                  95

Arg Val Leu His Asp Phe Gly Leu Asp Gly Tyr Arg Gly Tyr Ser Leu
            100                 105                 110

Ala Asp Trp Val Cys Leu Ala Tyr Phe Glu Ser Gly Phe Asn Ala Ala
        115                 120                 125
```

```
Ala Leu Asp Tyr Glu Ala Asp Gly Ser Thr Asp Tyr Gly Ile Phe Gln
        130                 135                 140

Ile Asn Ser Arg Arg Trp Cys Ser Asn Leu Thr Pro Asn Val Pro Asn
145                 150                 155                 160

Val Cys Arg Met Tyr Cys Ser Asp Leu Leu Asn Pro Asn Leu Lys Asp
                165                 170                 175

Thr Val Ile Cys Ala Met Lys Ile Thr Gln Glu Pro Gln Gly Leu Gly
            180                 185                 190

Tyr Trp Glu Ala Trp Arg His His Cys Gln Gly Lys Asp Leu Thr Glu
        195                 200                 205

Trp Val Asp Gly Cys Asp Phe
        210                 215

<210> SEQ ID NO 8
<211> LENGTH: 128
<212> TYPE: PRT
<213> ORGANISM: Homo sapiens

<400> SEQUENCE: 8

Lys Leu Tyr Gly Arg Cys Glu Leu Ala Arg Val Leu His Asp Phe Gly
  1               5                  10                  15

Leu Asp Gly Tyr Arg Gly Tyr Ser Leu Ala Asp Trp Val Cys Leu Ala
                 20                  25                  30

Tyr Phe Thr Ser Gly Phe Asn Ala Ala Ala Leu Asp Tyr Glu Ala Asp
             35                  40                  45

Gly Ser Thr Asp Asn Gly Ile Phe Gln Ile Asn Ser Arg Arg Trp Cys
 50                  55                  60

Ser Asn Leu Thr Pro Asn Val Pro Asn Val Cys Arg Met Tyr Cys Ser
65                  70                  75                  80

Asp Leu Leu Asn Pro Asn Leu Lys Asp Thr Val Ile Cys Ala Met Lys
                 85                  90                  95

Ile Thr Gln Glu Pro Gln Gly Leu Gly Tyr Trp Glu Ala Trp Arg His
            100                 105                 110

His Cys Gln Gly Lys Asp Leu Thr Glu Trp Val Asp Gly Cys Asp Phe
        115                 120                 125

<210> SEQ ID NO 9
<211> LENGTH: 138
<212> TYPE: PRT
<213> ORGANISM: Homo sapiens

<400> SEQUENCE: 9

Lys Ile Tyr Glu Arg Cys Glu Leu Ala Ala Arg Leu Glu Arg Ala Gly
  1               5                  10                  15

Leu Asn Gly Tyr Lys Gly Tyr Gly Val Gly Asp Trp Leu Cys Met Ala
                 20                  25                  30

His Tyr Glu Ser Gly Phe Asp Thr Ala Phe Val Asp His Asn Pro Asp
             35                  40                  45

Gly Ser Ser Glu Tyr Gly Ile Phe Gln Leu Asn Ser Ala Trp Trp Cys
 50                  55                  60

Asp Asn Gly Ile Thr Pro Thr Lys Asn Leu Cys His Met Asp Cys His
65                  70                  75                  80

Asp Leu Leu Asn Arg His Ile Leu Asp Asp Ile Arg Cys Ala Lys Gln
                 85                  90                  95

Ile Val Ser Ser Gln Asn Gly Leu Ser Ala Trp Thr Ser Trp Arg Leu
            100                 105                 110
```

```
His Cys Ser Gly His Asp Leu Ser Glu Trp Leu Lys Gly Cys Asp Met
            115                 120                 125

His Val Lys Ile Asp Pro Lys Ile His Pro
        130                 135

<210> SEQ ID NO 10
<211> LENGTH: 128
<212> TYPE: PRT
<213> ORGANISM: Homo sapiens

<400> SEQUENCE: 10

Lys Leu Tyr Gly Arg Cys Glu Leu Ala Arg Val Leu His Asp Phe Gly
  1               5                  10                  15

Leu Asp Gly Tyr Arg Gly Tyr Ser Leu Ala Asp Trp Val Cys Leu Ala
             20                  25                  30

Tyr Phe Glu Ser Gly Phe Asn Ala Ala Ala Leu Asp Tyr Glu Ala Asp
         35                  40                  45

Gly Ser Thr Asp Tyr Gly Ile Phe Gln Ile Asn Ser Arg Arg Trp Cys
 50                  55                  60

Ser Asn Leu Thr Pro Asn Val Pro Asn Val Cys Arg Met Tyr Cys Ser
65                  70                  75                  80

Asp Leu Leu Asn Pro Asn Leu Lys Asp Thr Val Ile Cys Ala Met Lys
                 85                  90                  95

Ile Thr Gln Glu Pro Gln Gly Leu Gly Tyr Trp Glu Ala Trp Arg His
            100                 105                 110

His Cys Gln Gly Lys Asp Leu Thr Glu Trp Val Asp Gly Cys Asp Phe
        115                 120                 125

<210> SEQ ID NO 11
<211> LENGTH: 138
<212> TYPE: PRT
<213> ORGANISM: Homo sapiens

<400> SEQUENCE: 11

Lys Ile Tyr Glu Arg Cys Glu Leu Ala Ala Arg Leu Glu Arg Ala Gly
  1               5                  10                  15

Leu Asn Gly Tyr Lys Gly Tyr Val Gly Asp Trp Leu Cys Met Ala
             20                  25                  30

His Tyr Glu Ser Gly Phe Asp Thr Ala Phe Val Asp His Asn Pro Asp
         35                  40                  45

Gly Ser Ser Asp Tyr Gly Ile Phe Gln Leu Asn Ser Ala Trp Trp Cys
 50                  55                  60

Asp Asn Gly Ile Thr Pro Thr Lys Asn Leu Cys His Met Asp Cys His
65                  70                  75                  80

Asp Leu Leu Asn Arg His Ile Leu Asp Ile Arg Cys Ala Lys Gln
                 85                  90                  95

Ile Val Ser Ser Gln Asn Gly Leu Ser Ala Trp Thr Ser Trp Arg Leu
            100                 105                 110

His Cys Ser Gly His Asp Leu Ser Glu Trp Leu Lys Gly Cys Asp Met
        115                 120                 125

His Val Lys Ile Asp Pro Lys Ile His Pro
        130                 135

<210> SEQ ID NO 12
<211> LENGTH: 126
<212> TYPE: PRT
<213> ORGANISM: Nasalis concolor
```

<400> SEQUENCE: 12

```
Lys Ile Phe Glu Arg Cys Glu Leu Ala Arg Thr Leu Lys Lys Leu Gly
 1               5                  10                  15

Leu Asp Gly Tyr Lys Gly Val Ser Leu Ala Asn Trp Val Cys Leu Ala
                20                  25                  30

Lys Trp Glu Ser Gly Tyr Asn Thr Glu Ala Thr Asn Tyr Asn Pro Asp
            35                  40                  45

Glu Ser Thr Asp Tyr Gly Ile Phe Gln Ile Asn Ser Arg Tyr Trp Cys
        50                  55                  60

Asn Asn Lys Thr Pro Gly Ala Val Asp Ala Cys His Ile Ser Cys Ser
 65                  70                  75                  80

Ala Leu Leu Gln Asn Asn Ile Ala Asp Ala Val Ala Cys Ala Lys Arg
                85                  90                  95

Val Val Ser Asp Pro Gln Gly Val Arg Ala Trp Val Ala Trp Arg Asn
               100                 105                 110

His Cys Gln Asn Lys Asp Val Ser Gln Tyr Val Lys Gly Cys
            115                 120                 125
```

<210> SEQ ID NO 13
<211> LENGTH: 126
<212> TYPE: PRT
<213> ORGANISM: Nasalis concolor

<400> SEQUENCE: 13

```
Lys Ile Phe Glu Arg Cys Glu Leu Ala Arg Thr Leu Lys Lys Leu Gly
 1               5                  10                  15

Leu Asp Gly Tyr Lys Gly Val Ser Leu Ala Asn Trp Val Cys Leu Ala
                20                  25                  30

Lys Trp Glu Ser Gly Tyr Asn Thr Glu Ala Thr Asn Tyr Asn Pro Asp
            35                  40                  45

Glu Ser Thr Asp Tyr Gly Ile Phe Gln Ile Asn Ser Arg Tyr Trp Cys
        50                  55                  60

Asn Asn Lys Thr Pro Gly Ala Val Asp Ala Cys His Ile Ser Cys Ser
 65                  70                  75                  80

Ala Leu Leu Gln Asn Asn Ile Ala Asp Ala Val Ala Cys Ala Lys Arg
                85                  90                  95

Val Val Ser Asp Pro Gln Gly Ile Arg Ala Trp Val Ala Trp Arg Asn
               100                 105                 110

His Cys Gln Asn Lys Asp Val Ser Gln Tyr Val Lys Gly Cys
            115                 120                 125
```

<210> SEQ ID NO 14
<211> LENGTH: 126
<212> TYPE: PRT
<213> ORGANISM: Macaca mulatta

<400> SEQUENCE: 14

```
Lys Ile Phe Glu Arg Cys Glu Leu Ala Arg Thr Leu Lys Lys Leu Gly
 1               5                  10                  15

Leu Asp Gly Tyr Lys Gly Val Ser Leu Ala Asn Trp Val Cys Leu Ala
                20                  25                  30

Lys Trp Glu Ser Gly Tyr Asn Thr Glu Ala Thr Asn Tyr Asn Pro Asp
            35                  40                  45

Glu Ser Thr Asp Tyr Gly Ile Phe Gln Ile Asn Ser Arg Tyr Trp Cys
        50                  55                  60

Asn Asn Lys Thr Pro Gly Ala Val Asp Ala Cys His Ile Ser Cys Ser
```

```
                65                  70                  75                  80
Ala Leu Leu Gln Asn Asn Ile Ala Asp Ala Val Ala Cys Ala Lys Arg
                        85                  90                  95

Val Val Ser Asp Pro Gln Gly Ile Arg Ala Trp Val Ala Trp Arg Asn
                    100                 105                 110

His Cys Gln Asn Arg Asp Val Ser Gln Tyr Val Lys Gly Cys
                115                 120                 125

<210> SEQ ID NO 15
<211> LENGTH: 126
<212> TYPE: PRT
<213> ORGANISM: Macaca mulatta

<400> SEQUENCE: 15

Lys Ile Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Val Cys Leu Ala
                 20                  25                  30

Lys Trp Glu Ser Asp Tyr Asn Thr Gln Ala Thr Asn Tyr Asn Pro Asp
             35                  40                  45

Gln Ser Thr Asp Tyr Gly Ile Phe Gln Ile Asn Ser His Tyr Trp Cys
         50                  55                  60

Asn Asn Lys Thr Pro Gly Ala Val Asn Ala Cys Arg Ile Ser Cys Asn
 65                  70                  75                  80

Ala Leu Leu Gln Asp Asn Ile Ala Asp Ala Val Thr Cys Ala Lys Arg
                     85                  90                  95

Val Val Arg Asp Pro Gln Gly Ile Arg Ala Trp Val Ala Trp Arg Asn
                    100                 105                 110

His Cys Gln Asn Arg Asp Val Ser Gln Tyr Val Gln Gly Cys
                115                 120                 125

<210> SEQ ID NO 16
<211> LENGTH: 126
<212> TYPE: PRT
<213> ORGANISM: Nasalis concolor

<400> SEQUENCE: 16

Lys Ile Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Val Cys Leu Ala
                 20                  25                  30

Lys Trp Glu Ser Gly Tyr Asn Thr Gln Ala Thr Asn Tyr Asn Pro Asp
             35                  40                  45

Gln Ser Thr Asp Tyr Gly Ile Phe Gln Ile Asn Ser His Tyr Trp Cys
         50                  55                  60

Asn Asn Lys Thr Pro Gly Ala Val Asn Ala Cys His Ile Ser Cys Asn
 65                  70                  75                  80

Ala Leu Leu Gln Asp Asn Ile Ala Asp Ala Val Thr Cys Ala Lys Arg
                     85                  90                  95

Val Val Arg Asp Pro Gln Gly Ile Arg Ala Trp Val Ala Trp Arg Asn
                    100                 105                 110

His Cys Gln Asn Arg Asp Val Ser Gln Tyr Val Gln Gly Cys
                115                 120                 125

<210> SEQ ID NO 17
<211> LENGTH: 126
<212> TYPE: PRT
```

-continued

<213> ORGANISM: Gorilla gorilla

<400> SEQUENCE: 17

```
Lys Val Phe Glu Arg Cys Glu Leu Ala Arg Thr Leu Lys Arg Leu Gly
  1               5                  10                  15

Met Asp Gly Tyr Arg Gly Ile Ser Leu Ala Asn Trp Met Cys Leu Ala
             20                  25                  30

Lys Trp Glu Ser Gly Tyr Asn Thr Arg Ala Thr Asn Tyr Asn Ala Asp
         35                  40                  45

Arg Ser Thr Asp Tyr Gly Ile Phe Gln Ile Asn Ser Arg Tyr Trp Cys
     50                  55                  60

Asn Asp Lys Thr Pro Gly Ala Val Asn Ala Cys His Leu Ser Cys Ser
 65                  70                  75                  80

Ala Leu Leu Gln Asp Asn Ile Ala Asp Ala Val Ala Cys Ala Lys Arg
                 85                  90                  95

Val Val Arg Asp Pro Gln Gly Ile Arg Ala Trp Val Ala Trp Arg Asn
            100                 105                 110

Arg Cys Gln Asn Arg Asp Val Arg Gln Tyr Val Gln Gly Cys
        115                 120                 125
```

<210> SEQ ID NO 18
<211> LENGTH: 126
<212> TYPE: PRT
<213> ORGANISM: Homo sapiens

<400> SEQUENCE: 18

```
Lys Val Phe Glu Arg Cys Glu Leu Ala Arg Thr Leu Lys Arg Leu Gly
  1               5                  10                  15

Met Asp Gly Tyr Arg Gly Ile Ser Leu Ala Asn Trp Met Cys Leu Ala
             20                  25                  30

Lys Trp Glu Ser Gly Tyr Asn Thr Arg Ala Thr Asn Tyr Asn Ala Asp
         35                  40                  45

Arg Ser Thr Asp Tyr Gly Ile Phe Gln Ile Asn Ser Arg Tyr Trp Cys
     50                  55                  60

Asn Asp Lys Thr Pro Gly Ala Val Asn Ala Cys His Leu Ser Cys Ser
 65                  70                  75                  80

Ala Leu Leu Gln Asp Asn Ile Ala Asp Ala Val Ala Cys Ala Lys Arg
                 85                  90                  95

Val Val Arg Asp Pro Gln Gly Ile Arg Ala Trp Val Ala Trp Arg Asn
            100                 105                 110

Arg Cys Gln Asn Arg Asp Val Arg Gln Tyr Val Gln Gly Cys
        115                 120                 125
```

<210> SEQ ID NO 19
<211> LENGTH: 126
<212> TYPE: PRT
<213> ORGANISM: Leporinus elongatus

<400> SEQUENCE: 19

```
Lys Ile Tyr Glu Arg Cys Glu Leu Ala Arg Thr Leu Lys Lys Leu Gly
  1               5                  10                  15

Leu Asp Gly Tyr Lys Gly Val Ser Leu Ala Asn Trp Met Cys Leu Ala
             20                  25                  30

Lys Trp Glu Ser Ser Tyr Asn Thr Arg Ala Thr Asn Tyr Asn Pro Asp
         35                  40                  45

Lys Ser Thr Asp Tyr Gly Ile Phe Gln Ile Asn Ser Arg Tyr Trp Cys
     50                  55                  60
```

```
Asn Asp Lys Thr Pro Arg Ala Val Asn Ala Cys His Ile Pro Cys Ser
 65                  70                  75                  80

Ala Leu Leu Lys Asp Asp Ile Thr Gln Ala Val Ala Cys Ala Lys Arg
                 85                  90                  95

Val Val Ser Asp Pro Gln Gly Ile Arg Ala Trp Val Ala Trp Arg Asn
            100                 105                 110

His Cys Gln Asn Gln Asp Leu Thr Pro Tyr Ile Arg Gly Cys
        115                 120                 125
```

```
<210> SEQ ID NO 20
<211> LENGTH: 126
<212> TYPE: PRT
<213> ORGANISM: Colobus guereza

<400> SEQUENCE: 20

Lys Ile Phe Glu Arg Cys Glu Leu Ala Arg Thr Leu Lys Lys Leu Gly
  1               5                  10                  15

Leu Asp Gly Tyr Lys Gly Val Ser Leu Ala Asn Trp Val Cys Leu Ala
             20                  25                  30

Lys Trp Glu Ser Gly Tyr Asn Thr Asp Ala Thr Asn Tyr Asn Pro Asp
         35                  40                  45

Glu Ser Thr Asp Tyr Gly Ile Phe Gln Ile Asn Ser Arg Tyr Trp Cys
 50                  55                  60

Asn Asn Lys Thr Pro Gly Ala Val Asn Ala Cys His Ile Ser Cys Asn
 65                  70                  75                  80

Ala Leu Leu Gln Asn Asn Ile Ala Asp Ala Val Ala Cys Ala Lys Arg
                 85                  90                  95

Val Val Ser Asp Pro Gln Gly Ile Arg Ala Trp Val Ala Trp Lys Lys
            100                 105                 110

His Cys Gln Asn Arg Asp Val Ser Gln Tyr Val Glu Gly Cys
        115                 120                 125
```

```
<210> SEQ ID NO 21
<211> LENGTH: 126
<212> TYPE: PRT
<213> ORGANISM: Macaca mulatta

<400> SEQUENCE: 21

Lys Ile Phe Glu Arg Cys Glu Leu Ala Arg Thr Leu Lys Arg Leu Gly
  1               5                  10                  15

Leu Asp Gly Tyr Arg Gly Ile Ser Leu Ala Asn Trp Val Cys Leu Ala
             20                  25                  30

Lys Trp Glu Ser Asn Tyr Asn Thr Gln Ala Thr Asn Tyr Asn Pro Asp
         35                  40                  45

Gln Ser Thr Asp Tyr Gly Ile Phe Gln Ile Asn Ser His Tyr Trp Cys
 50                  55                  60

Asn Asn Lys Thr Pro Gly Ala Val Asn Ala Cys His Ile Ser Cys Asn
 65                  70                  75                  80

Ala Leu Leu Gln Asp Asn Ile Ala Asp Ala Val Thr Cys Ala Lys Arg
                 85                  90                  95

Val Val Ser Asp Pro Gln Gly Ile Arg Ala Trp Val Ala Trp Arg Asn
            100                 105                 110

His Cys Gln Asn Arg Asp Val Ser Gln Tyr Val Gln Gly Cys
        115                 120                 125
```

```
<210> SEQ ID NO 22
```

```
<211> LENGTH: 128
<212> TYPE: PRT
<213> ORGANISM: Aythya americana

<400> SEQUENCE: 22

Lys Val Tyr Ser Arg Cys Glu Leu Ala Ala Met Lys Arg Leu Gly
 1               5                  10                  15

Leu Asp Asn Tyr Arg Gly Tyr Ser Leu Gly Asn Trp Val Cys Ala Ala
            20                  25                  30

Asn Tyr Glu Ser Gly Phe Asn Thr Gln Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asp Asn Gly Lys Thr Pro Arg Lys Asn Ala Cys Gly Ile Pro Cys Ser
65                  70                  75                  80

Val Leu Leu Arg Ser Asp Ile Thr Glu Ala Val Arg Cys Ala Lys Arg
                85                  90                  95

Ile Val Ser Asp Gly Asp Gly Met Asn Ala Trp Val Ala Trp Arg Asn
            100                 105                 110

Arg Cys Arg Gly Thr Asp Val Ser Lys Trp Ile Arg Gly Cys Arg Leu
        115                 120                 125

<210> SEQ ID NO 23
<211> LENGTH: 128
<212> TYPE: PRT
<213> ORGANISM: Phasianus colchicus

<400> SEQUENCE: 23

Lys Val Tyr Gly Arg Cys Glu Leu Ala Ala Ala Met Lys Arg Leu Gly
 1               5                  10                  15

Leu Asp Asn Tyr Arg Gly Tyr Ser Leu Gly Asn Trp Val Cys Ala Ala
            20                  25                  30

Lys Tyr Glu Ser Asn Phe Asn Thr His Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Lys Thr Pro Gly Arg Asn Leu Cys His Ile Pro Cys Ser
65                  70                  75                  80

Ala Leu Leu Ser Ser Asp Ile Thr Ala Ser Val Asn Cys Ala Lys Lys
                85                  90                  95

Ile Val Ser Asp Gly Asn Gly Met Asn Ala Trp Val Ala Trp Arg Asn
            100                 105                 110

Arg Cys Lys Gly Thr Asp Val Ser Val Trp Thr Arg Gly Cys Arg Leu
        115                 120                 125

<210> SEQ ID NO 24
<211> LENGTH: 128
<212> TYPE: PRT
<213> ORGANISM: Aythya americana

<400> SEQUENCE: 24

Lys Val Tyr Glu Arg Cys Glu Leu Ala Ala Ala Met Lys Arg Leu Gly
 1               5                  10                  15

Leu Asp Asn Tyr Arg Gly Tyr Ser Leu Gly Asn Trp Val Cys Ala Ala
            20                  25                  30

Asn Tyr Glu Ser Ser Phe Asn Thr Gln Ala Thr Asn Arg Asn Thr Asp
        35                  40                  45
```

```
Gly Ser Thr Asp Tyr Gly Ile Leu Glu Ile Asn Ser Arg Trp Trp Cys
        50                  55                  60

Asp Asn Gly Lys Thr Pro Arg Lys Asn Ala Cys Gly Ile Pro Cys Ser
 65                  70                  75                  80

Val Leu Leu Arg Ser Asp Ile Thr Glu Ala Val Lys Cys Ala Lys Arg
                 85                  90                  95

Ile Val Ser Asp Gly Asp Gly Met Asn Ala Trp Val Ala Trp Arg Asn
                100                 105                 110

Arg Cys Lys Gly Thr Asp Val Ser Arg Trp Ile Arg Gly Cys Arg Leu
            115                 120                 125
```

<210> SEQ ID NO 25
<211> LENGTH: 128
<212> TYPE: PRT
<213> ORGANISM: Phasianus colchicus

<400> SEQUENCE: 25

```
Lys Val Tyr Gly Arg Cys Glu Leu Ala Ala Ala Met Lys Arg Met Gly
 1               5                  10                  15

Leu Asp Asn Tyr Arg Gly Tyr Ser Leu Gly Asn Trp Val Cys Ala Ala
                 20                  25                  30

Lys Phe Glu Ser Asn Phe Asn Thr Gly Ala Thr Asn Arg Asn Thr Asp
             35                  40                  45

Gly Ser Thr Asp Tyr Gly Ile Leu Gln Ile Asn Ser Arg Trp Trp Cys
        50                  55                  60

Asn Asp Gly Arg Thr Pro Gly Lys Asn Leu Cys His Ile Pro Cys Ser
 65                  70                  75                  80

Ala Leu Leu Ser Ser Asp Ile Thr Ala Ser Val Asn Cys Ala Lys Lys
                 85                  90                  95

Ile Val Ser Asp Gly Asn Gly Met Asn Ala Trp Val Ala Trp Arg Lys
                100                 105                 110

His Cys Lys Gly Thr Asp Val Asn Val Trp Ile Arg Gly Cys Arg Leu
            115                 120                 125
```

<210> SEQ ID NO 26
<211> LENGTH: 128
<212> TYPE: PRT
<213> ORGANISM: Ortalis vetula

<400> SEQUENCE: 26

```
Lys Ile Tyr Lys Arg Cys Glu Leu Ala Ala Ala Met Lys Arg Tyr Gly
 1               5                  10                  15

Leu Asp Asn Tyr Arg Gly Tyr Ser Leu Gly Asn Trp Val Cys Ala Ala
                 20                  25                  30

Arg Tyr Glu Ser Asn Tyr Asn Thr Gln Ala Thr Asn Arg Asn Ser Asn
             35                  40                  45

Gly Ser Thr Asp Tyr Gly Ile Leu Gln Ile Asn Ser Arg Trp Trp Cys
        50                  55                  60

Asn Asp Gly Arg Thr Pro Gly Lys Asn Leu Cys His Ile Ser Cys Ser
 65                  70                  75                  80

Ala Leu Met Gly Ala Asp Ile Ala Pro Ser Val Arg Cys Ala Lys Arg
                 85                  90                  95

Ile Val Ser Asp Gly Asp Gly Met Asn Ala Trp Val Ala Trp Arg Lys
                100                 105                 110

His Cys Lys Gly Thr Asp Val Ser Thr Trp Ile Lys Asp Cys Lys Leu
            115                 120                 125
```

<210> SEQ ID NO 27
<211> LENGTH: 128
<212> TYPE: PRT
<213> ORGANISM: Phasianus colchicus

<400> SEQUENCE: 27

Lys Val Tyr Gly Arg Cys Glu Leu Ala Ala Ala Met Lys Arg Met Gly
1               5                   10                  15

Leu Asp Asn Tyr Arg Gly Tyr Ser Leu Gly Asn Trp Val Cys Ala Ala
            20                  25                  30

Lys Phe Glu Ser Asn Phe Asn Thr Gly Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Lys Asn Leu Cys His Ile Pro Cys Ser
65                  70                  75                  80

Ala Leu Leu Ser Ser Asp Ile Thr Ala Ser Val Asn Cys Ala Lys Lys
                85                  90                  95

Ile Val Ser Asp Gly Asp Gly Met Asn Ala Trp Val Ala Trp Arg Lys
            100                 105                 110

His Cys Lys Gly Thr Asp Val Asn Val Trp Ile Arg Gly Cys Arg Leu
        115                 120                 125

<210> SEQ ID NO 28
<211> LENGTH: 128
<212> TYPE: PRT
<213> ORGANISM: Phasianus colchicus

<400> SEQUENCE: 28

Lys Val Tyr Gly Arg Cys Glu Leu Ala Ala Ala Met Lys Arg Leu Gly
1               5                   10                  15

Leu Asp Asn Tyr Arg Gly Tyr Ser Leu Gly Asn Trp Val Cys Ala Ala
            20                  25                  30

Lys Phe Glu Ser Asn Phe Asn Thr His Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Arg Asn Leu Cys His Ile Pro Cys Ser
65                  70                  75                  80

Ala Leu Leu Ser Ser Asp Ile Thr Ala Ser Val Asn Cys Ala Lys Lys
                85                  90                  95

Ile Val Ser Asp Gly Asn Gly Met Asn Ala Trp Val Ala Trp Arg Asn
            100                 105                 110

Arg Cys Lys Gly Thr Asp Val Asn Ala Trp Thr Arg Gly Cys Arg Leu
        115                 120                 125

<210> SEQ ID NO 29
<211> LENGTH: 128
<212> TYPE: PRT
<213> ORGANISM: Phasianus colchicus

<400> SEQUENCE: 29

Lys Val Tyr Gly Arg Cys Glu Leu Ala Ala Ala Met Lys Arg Leu Gly
1               5                   10                  15

Leu Asp Asn Tyr Arg Gly Tyr Ser Leu Gly Asn Trp Val Cys Ala Ala
            20                  25                  30

Lys Phe Glu Ser Asn Phe Asn Thr His Ala Thr Asn Arg Asn Thr Asp

```
                35                  40                  45
Gly Ser Thr Asp Tyr Gly Ile Leu Gln Ile Asn Ser Arg Trp Trp Cys
    50                  55                  60

Asn Asp Gly Arg Thr Pro Gly Arg Asn Leu Cys His Ile Ser Cys Ser
65                  70                  75                  80

Ala Leu Leu Ser Ser Asp Ile Thr Ala Ser Val Asn Cys Ala Lys Lys
                85                  90                  95

Ile Val Ser Asp Arg Asn Gly Met Asn Ala Trp Val Ala Trp Arg Asn
                100                 105                 110

Arg Cys Lys Gly Thr Asp Val Asn Ala Trp Ile Arg Gly Cys Arg Leu
            115                 120                 125

<210> SEQ ID NO 30
<211> LENGTH: 128
<212> TYPE: PRT
<213> ORGANISM: Macaca mulatta

<400> SEQUENCE: 30

Lys Ile Phe Glu Arg Cys Glu Leu Ala Arg Thr Leu Lys Lys Leu Gly
1               5                   10                  15

Leu Asp Gly Tyr Lys Gly Val Ser Leu Ala Asn Trp Val Cys Leu Ala
                20                  25                  30

Lys Trp Glu Ser Gly Tyr Asn Thr Glu Ala Thr Asn Tyr Asn Pro Asp
            35                  40                  45

Glu Ser Thr Asp Tyr Gly Ile Phe Gln Ile Asn Ser Arg Tyr Trp Cys
    50                  55                  60

Asn Asn Gly Lys Thr Pro Gly Val Asp Ala Cys His Ile Ser Cys Ser
65                  70                  75                  80

Ala Leu Leu Gln Asn Asn Ile Ala Asp Ala Val Ala Cys Ala Lys Arg
                85                  90                  95

Val Val Ser Asp Pro Gln Gly Ile Arg Ala Trp Val Ala Trp Arg Asn
                100                 105                 110

His Cys Gln Asn Arg Asp Val Ser Gln Tyr Val Lys Gly Cys Gly Val
            115                 120                 125

<210> SEQ ID NO 31
<211> LENGTH: 128
<212> TYPE: PRT
<213> ORGANISM: Nasalis concolor

<400> SEQUENCE: 31

Lys Ile Phe Glu Arg Cys Glu Leu Ala Arg Thr Leu Lys Lys Leu Gly
1               5                   10                  15

Leu Asp Gly Tyr Lys Gly Val Ser Leu Ala Asn Trp Val Cys Leu Ala
                20                  25                  30

Lys Trp Glu Ser Gly Tyr Asn Thr Glu Ala Thr Asn Tyr Asn Pro Asp
            35                  40                  45

Glu Ser Thr Asp Tyr Gly Ile Phe Gln Ile Asn Ser Arg Tyr Trp Cys
    50                  55                  60

Asn Asn Gly Lys Thr Pro Gly Val Asp Ala Cys His Ile Ser Cys Ser
65                  70                  75                  80

Ala Leu Leu Gln Asn Asn Ile Ala Asp Ala Val Ala Cys Ala Lys Arg
                85                  90                  95

Val Val Ser Asp Pro Gln Gly Ile Arg Ala Trp Val Ala Trp Arg Asn
                100                 105                 110
```

-continued

```
His Cys Gln Asn Lys Asp Val Ser Gln Tyr Val Lys Gly Cys Gly Val
        115                 120                 125
```